United States Patent [19]

Benz et al.

[11] Patent Number: 4,535,083
[45] Date of Patent: Aug. 13, 1985

[54] CLEAVAGE PRODUCTS OF 4',6'-DIDESOXY-4'-THIO-,6'-AMINO-HEPTURONIC ACID NUCLEOSIDES

[75] Inventors: Günter Benz, Velbert-Neviges; Karl G. Metzger, Wuppertal-Elberfeld; Hans-Joachim Zeiler, Velbert-Neviges, all of Fed. Rep. of Germany

[73] Assignee: Bayer Aktiengesellschaft, Leverkusen, Fed. Rep. of Germany

[21] Appl. No.: 530,835

[22] Filed: Sep. 9, 1983

[30] Foreign Application Priority Data

Oct. 1, 1982 [DE] Fed. Rep. of Germany ....... 3236389

[51] Int. Cl.³ ................. A61K 31/505; C07D 239/47; C07D 239/54
[52] U.S. Cl. .................... 514/274; 544/309; 544/312; 544/317; 435/69; 435/118
[58] Field of Search ........... 544/309, 312, 317; 424/251; 435/69, 118

[56] References Cited

U.S. PATENT DOCUMENTS 3,639,259  2/1972  Scarpelli .................... 435/69
4,415,557 11/1983  Metzger et al. ............. 260/112.5 R
4,416,870 11/1983  Metzger et al. ............. 260/112.5 R Primary Examiner—Donald G. Daus
Assistant Examiner—Stephen Kapner
Attorney, Agent, or Firm—Sprung, Horn, Kramer & Woods

[57] ABSTRACT

The invention relates to compounds of the formula

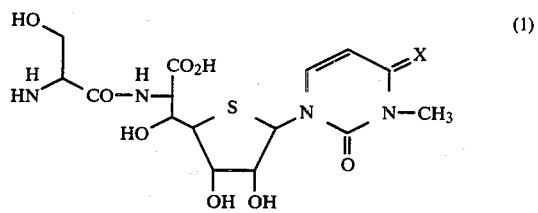

said compounds being obtainable by cleavage of compounds of formula

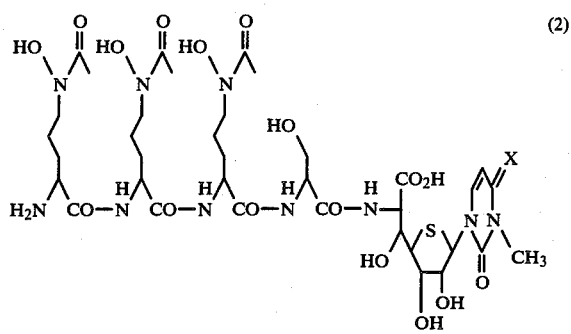

The compounds of the invention as well as compositions and medicaments containing a compound of the invention are useful as antimicrobial agents.

13 Claims, No Drawings

CLEAVAGE PRODUCTS OF 4',6'-DIDESOXY-4'-THIO-,6'-AMINO-HEPTURONIC ACID NUCLEOSIDES

DE-OS (German Published Specification) Nos. 3,102,136 and 3,102,137 corresponding respectively to U.S. Ser. No. 340,418 filed Jan. 18, 1982 now U.S. Pat. No. 4,416,870 and U.S. Ser. No. 340,449 filed Jan. 18, 1982 now U.S. Pat. No. 4,415,557, disclose 4', 6'-didesoxy-4'-thio-6'-amino-hepturonic acid nucleosides. These compounds have an antibiotic action.

The present invention makes available compounds of the formula

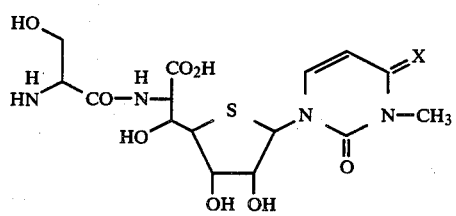

in which X is N—CO—NH$_2$ or 0.

The compounds according to the invention can be obtained by cleaving compounds of the formula 2

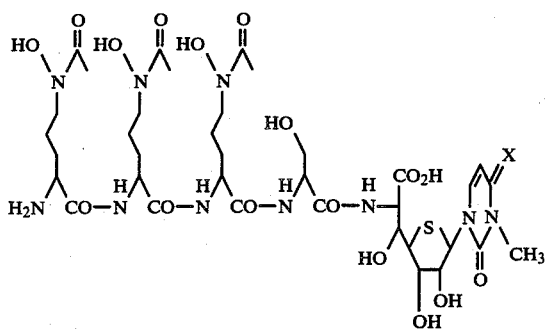

The compounds of the formula 2 and their preparation are described in the Offenlegungschriften (Published Specification Nos. 3,102,136 and 3,102,137) mentioned at the outset and at the corresponding EP-A Nos. 57,349 and 57,812.

The cleavage of these compounds to give the compounds according to the invention is preferably carried out enzymatically. Peptide hydrolases of the groups comprising EC 3.4.11,α-aminoacyl-peptide hydrolases and EC 3.4.21-23 proteases are particularly suitable for this purpose. Among these, the leucine aminopeptidase (pigs' kidney, microsomal), α-chymotrypsin, subtilisin, aminoacylase I, β-lactamase from $E.$ $coli$ T7, proteinase K and pronase E may be particularly mentioned.

The optimum cleavage conditions in each case can be readily determined by simple experiments in aqueous buffer solutions. In particular, the reaction times required depend on the enzyme used. Thus, for example, cleavage with the particularly preferred pigs' liver leucine aminopeptidase can be carried out at 25° C. in the course of 40 hours, while, for example, with the particularly preferred microsomal leucine aminopeptidase (1 mmol of substrate, 29.3 U, U=Unit Definition: One unit will hydrolyse 1.0 μm of L-leucinamide to L-leucine and NH$_3$ per minute at pH 8.5 at 25° C.), cleavage takes place in the course of 16 hours at pH 7.2 and 37° C.

Very generally, it can be stated that the reaction times are about 10-50 hours, preferably 15-40 hours, and the reaction temperature is about 20°-40° C. The cleavage is preferably carried out in the presence of a buffer, at pH values of 7-9.

Directly after the reaction, the particular compound according to the invention is separated off from any other cleavage products which are present, that is to say it is purified.

The purification is preferably carried out by chromatography. It is preferably carried out over cellulose ion exchangers (e.g. Sephadex SP 25 H⊕, sodium chloride gradient as the mobile phase), adsorber resins and silica gel.

The compounds according to the invention surprisingly exhibit antimicrobial activity, which is demonstrated by in vitro experiments.

In the in vitro agar dilution test according to the internationally customary test (American National Committee for Clinical Laboratory Standards=NCCLS), activity is found against the germs listed below.

TABLE 1

| Compound | Germ | MIC (μg/ml) |
|---|---|---|
| 1 X = NCONH$_2$ | $E.$ $coli$ Neumann | 32 |
|  | Klebs. 57 USA | 4 |
|  | Staph. epid. 25185 | 64 |
| 1 X = O | Serratia 16001 | 128 |

The minimum inhibitory concentration (MIC) was determined by the agar dilution procedure, using an inoculator and an inoculation density of $10^4$ per inoculation point. The MIC is the concentration at which no bacteria colonies grow.

The compounds according to the invention, particularly in the form of pharmaceutical compositions, can therefore be used in combating bacterial diseases. Such pharmaceutical preparations consist of at least one of the active compounds according to the invention and, if appropriate, suitable inert non-toxic excipients and auxiliaries. The present invention also includes such pharmaceutical preparations.

The present invention also includes pharmaceutical preparations in dosage units. This means that the preparations are in the form of individual parts, for example tablets, dragées, capsules, pills, suppositories and ampoules, of which the content of active substance correspond to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, pharmaceutically suitable excipients there are to be understood solid, semi-solid or liquid diluents, fillers and formulation auxiliaries of all kinds.

Tablets, dragées, capsules, pills, granules, suppositories, solutions, suspensions and emulsions, pastes, ointments, gels, creams, lotions, powders and sprays may be mentioned as preferred pharmaceutical preparations.

Tablets, dragées, capsules, pills and granules can contain the active compound or compounds alongside the customary excipients such as (a) fillers and extenders, for example starches, lactose, sucrose, glucose, mannitol and silica, (b) binders, for example carboxymethylcellulose. Alginates, gelatine and polyvinylpyrrolidone, (c)

humectants, for example glycerol, (d) disintegrating agents, for example agar-agar, calcium carbonate and sodium carbonate, (e) solution retarders, for example paraffin, and (f) resorption accelerators, for example quaternary ammonium compounds, (g) wetting agents, for example acetyl alcohol or glycerol monostearate, (h) adsorbents, for example kaolin and bentonite, and (i) lubricants, for example talc, calcium stearate and magnesium stearate and solid polyethylene glycols or mixtures of the substances listed under (a) to (i).

The tablets, dragées, capsules, pills and granules can be provided with the customary coatings and shells optionally containing opacifying agents and can also be of such composition that they release the active compound only, or preferentially, in a certain part of the intestinal tract, optionally in a delayed manner, examples of embedding compositions which can be used being polymeric substances and waxes.

The active compound, optionally together with one or more of the abovementioned excipients, can also be in a micro-encapsulated form.

Suppositories can contain, in addition to the active compound, the customary water-soluble or water-insoluble excipients, for example polyethylene glycols, fats, for example cacao fat, and higher esters (for example $C_{14}$-alcohol with $C_{16}$-fatty acid) or mixtures of these substances.

Ointments, pastes, creams and gels can contain, in addition to the active compound, the customary excipients, for example animal and vegetable fats, waxes, paraffins, starch, tragacanth, cellulose derivatives, polyethylene glycol, silicones, bentonites, silica, talc and zinc oxide or mixtures of these substances. Powders and sprays can contain, in addition to the active compound, the customary excipients, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain, in addition to the active compound, the customry excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerol-formal, tetrahydrofurfuryl alcohol, polyethylene glycols and fatty acid esters of sorbitane, or mixtures of these substances.

For parenteral administration, the solutions and emulsions can also be in a sterile form which is isotonic with blood.

Suspensions can contain, in addition to the active compound, the customary excipients, such as liquid diluents, for example water, ethyl alcohol or propylene glycol, suspending agents, for example ethoxylated isostearyl alcohols, polyoxyethylene sorbitol esters and sorbitane esters, microcrystalline cellulose, aluminium meta-hydroxide, bentonite, agar-agar and tragacanth or mixtures of these substances.

The formulation forms mentioned can also contain dyestuffs, preservatives and additives which improve the odour and flavour, for example peppermint oil and eucalyptus oil, and sweeteners, for example saccharin.

The compounds according to the invention should preferably be present in the abovementioned pharmaceutical preparations in a concentration of about 0.1 to 99.5, preferably of about 0.5 to 95, percent by weight of the total mixture.

The abovementioned pharmaceutical preparations can also contain other pharmaceutical active compounds in addition to the active compound according to the invention.

The abovementioned pharmaceutical preparations are manufactured in the usual manner according to known methods, for example by mixing the active compound with the excipient or excipients.

The present invention also includes the use of the compounds according to the invention and of pharmaceutical preparations which contain the active compound according to the invention, in medicine, for the treatment of bacterial diseases.

The active compound or the pharmaceutical preparations can be administered locally, orally, parenterally, intraperitoneally and/or rectally, preferably orally and parenterally, in particularly intramuscularly or intravenously, if appropriate also as a continuous intravenous drip.

In general it is advisable in the case of oral or parenteral administration to administer the active compounds according to the invention in total amounts of about 10 to 1000, preferably 50 to 600, mg/kg of body weight every 24 hours, optionally in the form of several individual administrations, in order to achieve the desired results. An individual administration preferably contains the active compounds according to the invention in amounts of about 50 to about 300 mg/kg, in particular 100 to 200 mg/kg, of body weight.

However, it can be necessary to deviate from the dosages mentioned and in particular to do so as a function of the nature and the severity of the illness, the nature of the preparation and of the administration of the medicine, and the time or interval over which the administration takes place. Thus it can suffice in some cases to manage with less than the abovementioned amount of active compound whilst in other cases the abovementioned amount of active compound must be exceeded. The particular required optimum dosage and the type of administration of the active compounds can easily be determined by anyone skilled in the art, on the basis of his expert knowledge.

The compounds according to the invention can furthermore be used as intermediate products for the preparation of other compounds, for example other active compounds. Thus, if derivatives of the compounds according to the Offenlegungsschriften (German Published Specifications DE-OS Nos. 3,102,136 and 3,102,137) mentioned at the outset are desired but this is difficult to achieve owing to the complexity of the molecule, it is possible, for example, to carry out the derivatisation on the compounds according to the invention instead, and then to recombine the resulting derivatives with the radical which has been split off. Such recombination can be achieved with suitable derivatives of amino acids oe peptides, respectively, with methods which are conventional in peptide chemistry.

EXAMPLES

EXAMPLE 1

Nucleoside 1 X=N—CO—NH₂

500 mg (0.5 mmol) of the compound of the formula

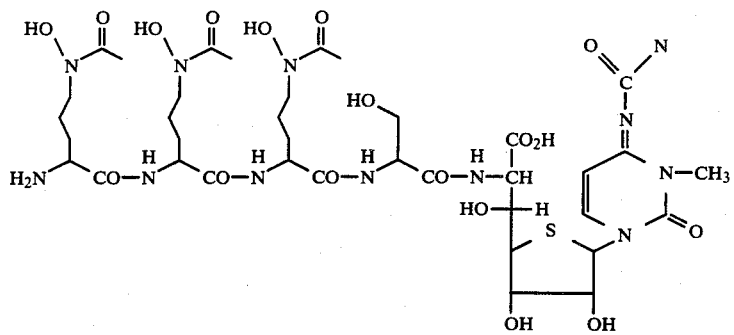

obtained as described below according to the working examples such as Example 1 of U.S. Ser. No. 340,449 filed Jan. 18, 1982 and now U.S. Pat. No. 4,415,557 dated Nov. 15, 1983, were dissolved in 250 ml of redistilled water, and the solution was adjusted to pH 8.5 with 0.5N tris buffer. 0.35 ml (175 U) of leucine aminopeptidase (pigs' kidney; Böhringer 107 182; specific activity 100 U/mg, 25° C. leucinamide as substrate) was added to this solution, and the mixture was stirred for 40 hours at 25° C. After neutralisation with 1N HCl, the mixture was freeze-dried, and chromatographed over 50 ml of Sephadex SP 25 H⊕ (first runnings 300 ml of redistilled water, 900 ml of gradient 0.01 N−0.09 N NaCl solution, rate of flow 2 ml/min.). 0.05 N Sörenson buffer was pumped into the eluate so that the fractions collected had a pH of 6.7. After HPLC (NH2-column 5 um; 4×250 mm Merck 50376, mobile phase: methanol/citric acid buffer, pH 4; 85:15 V/V; flow rate 2 ml/min) and thin-layer A: TLCOpti-RP $C_{12}$, Fluka, 1 n $(NH_4)CO_3$; B: TLC silica gel 60 F 254, Merck, acetonitrile: $H_2O$ 8:2; C: TLC silica gel 60 F 254, Merck, citric acid buffer pH 5: acetonitrile 5% $FeCl_3/H_2O$ 85:15:0.1, chromatographic analysis, the identical fractions were combined, and desalted over LGP 4067, and adsorbing Lewatit ® resin of Bayer AG, Germany.

HPLC and thin-layer chromatographic analysis, the identical fractions were combined, and desalted over LGP 4067.

| Fractions | 64–76 | 30.2 mg | |
|---|---|---|---|
| Fractions | 77–130 | 37.8 mg | |
| Fractions | 131–164 | 110.8 mg | 46.6% |

$^1$H-NMR ($D_2O$, 250 MHz): δ=3.35 (s; 3H, N—CH3), 3.78 (dd, J=6.0 Hz, J=4.4 Hz; 1H, H-4'); 3.96 (dd, J=12.2 Hz, J=5.6 Hz; 1H, O-C$\overline{H}$ serine); 4.04 (dd, J=12.2 Hz, J=4.3 Hz; 1H, O-C$\overline{H}$ serine); 4.21 (dd, J=5.6 Hz, J=4.3 Hz, 1H, N-CH serine); 4.34–4.54 (m; 4H, H-2',3',5',6'); 5.94 (d, J=5.3 Hz; 1H, H-1'), 6.20 (d, J=8.3 Hz; 1H, H-5), 8.26 (d, J=8.3 Hz, 1H, H-6).

UV (qualitative 0.1 N HCl)$\lambda_{max}$=304 nm.

The procedure of Example 1 of U.S. Ser. No. 340,449 reads as follows:

(a) The nutrient solution in which the production strain Streptomyces spec. WS 116 was cultivated in the pre-cultures was composed of 1% by weight of glucose, 1.3% of yeast extract, 0.05% of polyol and tap water. The pH was adjusted to 7.0 before the sterilisation. 4×1000 ml Erlenmeyer flasks, each of which contained 150 ml of this nutrient solution, were inoculated with the production strain and were incubated for 4 days at 28° C. on a rotary shaking machine at 220 revolutions/minute. A second pre-culture, a laboratory ferment which contained 20 liters of the above-mentioned nutrient solution, was inoculated with these pre-cultures and was incubated at 200 revolutions/minute, 10 liter of air/minute and 28° C. for 2 days. A production fermenter was inoculated with 20 liters of this culture, the production fermenter containing 600 liters of nutrient solution having the following composition: 0.7% by weight of citric acid, 0.8% of yeast extract, 0.2% of de-fatted soya bean flour, 0.2% of corn-steep liquor and 0.05% of silicone in tap water. The pH of this nutrient solution was adjusted to 6.4 with potassium hydroxide solution, before the sterilisation. The incubation of the production culture was effected over 2 to 4 days at 26° C., at a stirring rate of 50 revolutions/minute and an aeration of only 90 liters of air/minute. The fermentation was stopped at an optimum antibiotic inhibitory activity of the culture.

(b) 2×150 ml of the preculture were grown as indicated in Example 1a). These precultures were used for inoculating a 10 liter production fermenter, the nutrient solution of which, prepared in tap water, contained the following composition: 0.7% by weight of citric acid, 0.8% by weight of yeast extract, 0.2% by weight of defatted soya bean flour, 0.2% by weight of corn-steep liquor, 0.3% by weight of L-ornithine, 0.1% by weight of L-serine and 0.05% by weight of silicone.

All constituents, except for ornithine and serine, were sterilised, as customary, in the culture vessel. A pH value of 6.4 was established before the sterilisation. Ornithine and serine, dissolved in distilled $H_2O$, were added, after sterile filtration, to the mixture.

The incubation of the production culture was effected over 2 to 4 days at 26° C., at a stirring rate of 200 revolutions/minute and an aeration of only 1.5 liters of air/minute. The fermentation was stopped at an optimum antibiotic inhibitory activity of the supernatant liquor of the culture.

Example 2

Nucleoside 1 X=0

In each of two parallel experiments, 1.5 g (1.6 mmols) of the compound of the formula

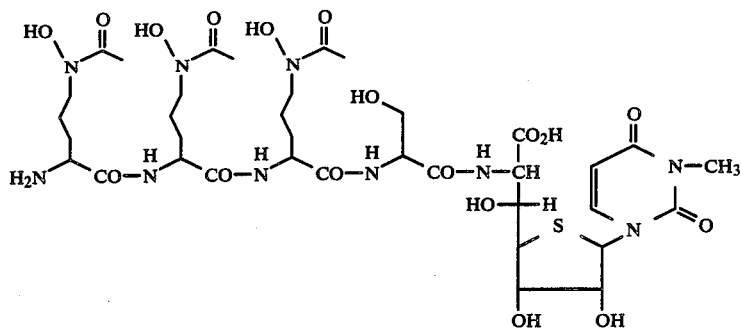

(A)

obtained as described below according to the working examples such as Example 1 of U.S. Ser. No. 340,418 filed Jan. 18, 1982 and now U.S. Pat. No. 4,416,870, issued Nov. 22, 1983, were dissolved in 500 ml of redistilled water, and the solution was adjusted to pH 7.2 with 0.5 N tris buffer. 0.75 ml (46.9 U) of leucine aminopeptidase (microsomal; Sigma L 5006, specific activity 10–20 U/mg, 37° C., leucinamid as substrate) was added to each of the solutions, and the mixtures were stirred for 16 hours at 37° C. The reaction solutions were combined and freeze-dried.

The crude substance was desalted over 600 ml of LGP 4067. Washing with redistilled water was carried out until UV-active material had been eluted. The remaining product was eluted with methanol/water 1:1.

| Fractions | 17–45 | 3.2 g | salt |
|---|---|---|---|
| Fractions | 71–74 | 0.2115 g | |
| Fractions | 75–120 | 1.2342 g | 90.2% |

H-NMR (D$_2$O, 250 MHz):=3.28 (s; 3H, N—CH$_3$); 3.96 (dd, J=12.5 Hz, J=6.0 Hz; O—CH serine), 4.03 (dd, J=12.5 Hz, J=5.0 Hz, 1H, O—CH serine); 4.20 (t, J=5 Hz; 1H, N—CH-serine); 4.43–4.51 (m;3H, H-2', 5'); 4.55 (d, J=5.5 Hz, 1H, H-6'), 5.93 (d, J=5.0 Hz, 1H, H-1'), 5.96 (d, J=8.0 Hz; 1H, H-5); 8.45 (d, J=8 Hz; 1H, H-6).

UV (qualitative, 0.1 N HCl)λ$_{max}$=264 nm.

The procedure of Example 1 of U.S. Ser. No. 340,418 reads as follows:

(a) The nutrient solution in which the production strain Streptomyces spec. WS 116 was cultivated in the precultures was composed of 1% by weight of glucose, 1.3% of yeast extract, 0.05% of polyol and tapwater. The pH was adjusted to 7.0 before the sterilisation. 4×1000 ml Erlenmeyer flasks, each of which contained 150 ml of this nutrient solution, were inoculated with the production strain and were incubated for 4 days at 28° C. on a rotary shaking machine at 220 revolutions/minute. A second preculture in a laboratory fermenter, which contained 20 liters of the above mentioned nutrient solution, was inoculated with these precultures and incubated for 2 days at 200 revolutions/minute, 10 liters of air/minute at 28° C. 20 liters of this culture were used for inoculating a production fermenter which contained 600 liters of nutrient solution with the following composition: b 0.7% by weight of citric acid, 0.8% of yeast extract, 0.2% of de-fatted soya bean flour, 0.2% of corn-steep liquor and 0.05% of silicone in tap water. The pH of this nutrient solution was adjusted, before the sterilisation to 6.4 using potassium hydroxide solution. The incubation of the production culture was effected over 2 to 4 days at 26° C. and at a stirring rate of 50 revolutions/minute and an aeration of only 90 liters of air/minute. The fermentation was stopped at the optimum antibiotic inhibitory activity of the culture.

(b) 2×150 ml of the preculture were grown as indicated in Example 1a). These precultures were used for inoculating 10 liter production fermenter, the nutrient solution of which, prepared in tap water, contained the following composition: 0.7% by weight of citric acid, 0.8% by weight of yeast extract, 0.2% by weight of de-fatted soya bean flour, 0.2% by weight of corn-steep liquor, 0.3% by weight of L-ornithine, 0.1% by weight of L-serine and 0.05% by weight of silicone.

All constituents except ornithine and serine were sterilised, as customary, in the culture vessel. A pH value of 6.4 was established before the sterilisation. Ornithine and serine, dissolved in distilled H$_2$O, were added to the mixture in a sterile-filtered form.

The incubation of the production culture was effected over 2 to 4 days at 26°, at a stirring rate of 200 revolutions/minute and an aeration of only 1.5 liters of air/minute. The fermentation was stopped at the optimum antibiotic inhibitory activity of the supernatant culture liquor.

We claim:

1. A compound of the formula 1

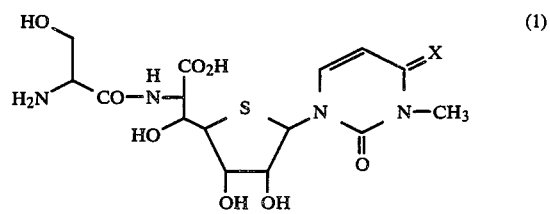

(1)

in which X is N—CO—NH$_2$ or 0.

2. A compound of claim 1 in which X is N—CO—NH$_2$.

3. A compound of claim 1 in which X is O.

4. A pharmaceutical composition containing as an active ingredient an antimycrobially effective amount of a compound according to claim 1 in admixture with an inert pharmaceutical carrier.

5. A pharmaceutical composition of claim 4 in the form of a sterile or physiologically isotomic aqueous solution.

6. A composition according to claim 4 containing from 0.5 to 95% by weight of the said active ingredient.

7. A medicament in dosage unit form comprising an antimycrobially effective amount of a compound according to claim 1 and an inert pharmaceutical carrier.

8. A medicament of claim 7 in the form of tablets, pills, dragées, capsules, ampoules or suppositories.

9. A method of combating bacterial infection in warm-blooded animals which comprises administering to said animals an antibacterially effective amount of an active compound according to claim 1 either alone or in admixture with an inert pharmaceutical carrier or in the form of a medicament.

10. A method according to claim 9 in which the active compound is administered in an amount of about 10 to 1000 mg per kg body weight per day.

11. A method according to claim 9 in which the active compound is administered in an amount of about 50 to 600 mg per kg body weight per day.

12. A method according to claim 10 in which the active compound is administered orally or parenterally.

13. A method according to claim 11 in which the active compound is administered orally or parenterally.

* * * * *

UNITED STATES PATENT AND TRADEMARK OFFICE
CERTIFICATE OF CORRECTION

PATENT NO. : 4,535,083
DATED : August 13, 1985
INVENTOR(S) : Günter Benz, et al.

It is certified that error appears in the above-identified patent and that said Letters Patent is hereby corrected as shown below:

| | |
|---|---|
| Col. 4, line 61 | After "acids" delete "oe" and substitute --or-- |
| Col. 5, line 1 | End of formula delete $"\underset{C}{\overset{O\diagdown \diagup N}{\phantom{C}}}"$ and substitute $--\underset{C}{\overset{O\diagdown \diagup NH_2}{\phantom{C}}}--$ |
| Col. 5, line 33 | Delete "0.05" and substitute --0.5-- |
| Col. 5, line 33 | Correct spelling of "Sörensen" |
| Col. 5, line 39 | After "(NH$_4$)" insert --$_2$-- |
| Col. 6, line 26 | Delete "ferment" and substitute --fermenter-- |
| Col. 7, line 22 | Correct spelling of "leucinamide" |
| Col. 7, line 63 | Before "0.7%" delete "b" |

Signed and Sealed this

Third Day of December 1985

[SEAL]

Attest:

DONALD J. QUIGG

Attesting Officer  Commissioner of Patents and Trademarks